(12) United States Patent
Johnson et al.

(10) Patent No.: US 11,891,548 B1
(45) Date of Patent: Feb. 6, 2024

(54) PROCESS FOR CONCENTRICALLY BONDING TUBES USING A HOT MELT ADHESIVE

(71) Applicant: MDCM Solutions, LLC, Maple Grove, MN (US)

(72) Inventors: Scott T. Johnson, Anoka, MN (US); Frank Smaron, Maple Plain, MN (US); Steve Leseman, Rogers, MN (US)

(73) Assignee: MDCM SOLUTIONS, LLC, Maple Grove, MN (US)

( * ) Notice: Subject to any disclaimer, the term of this patent is extended or adjusted under 35 U.S.C. 154(b) by 296 days.

(21) Appl. No.: 17/556,840

(22) Filed: Dec. 20, 2021

(51) Int. Cl.
| | |
|---|---|
| *A61M 25/00* | (2006.01) |
| *B29C 48/151* | (2019.01) |
| *B29C 63/18* | (2006.01) |
| *B29C 63/34* | (2006.01) |
| *B29C 63/48* | (2006.01) |
| *B29C 65/48* | (2006.01) |
| *C09J 5/02* | (2006.01) |
| *C09J 5/06* | (2006.01) |

(Continued)

(52) U.S. Cl.
CPC ............ *C09J 5/06* (2013.01); *A61M 25/0009* (2013.01); *A61M 25/0045* (2013.01); *B29C 48/0021* (2019.02); *B29C 48/151* (2019.02); *B29C 63/0017* (2013.01); *B29C 63/18* (2013.01); *B29C 63/34* (2013.01); *B29C 65/4815* (2013.01); *B29C 66/026* (2013.01); *B29C 66/5221* (2013.01); *B29C 66/52272* (2013.01); *C09J 5/02* (2013.01); *C09J 127/18* (2013.01); *C09J 153/00* (2013.01); *C09J 175/04* (2013.01); *A61M 2025/0062* (2013.01); *A61M 2205/0222* (2013.01); *B29C 2063/483* (2013.01)

(58) Field of Classification Search
CPC .......... A61M 25/0009; A61M 25/0043; A61M 25/0045; A61M 2025/0046; A61M 2025/0047; A61M 2025/0062; A61M 2205/0222; B29C 48/0021; B29C 48/0022; B29C 48/15; B29C 48/151; B29C 48/34; B29C 63/0017; B29C 63/18; B29C 63/34; B29C 2063/483; B29C 2063/485; B29C 65/481; B29C 65/4815; B29C 66/02; B29C 66/026; B29C 66/112; B29C 66/1122; B29C 66/5221; B29C 66/52271; B29C 66/52272; B29C 66/742; B29C 66/7428; B29C 66/74283; B29C 66/74285; B29C 69/008; B29C 2793/0027; C09J 5/02; C09J 5/06; C09J 127/18; C09J 153/00; C09J 175/04
See application file for complete search history.

(56) References Cited

U.S. PATENT DOCUMENTS

| | | | | |
|---|---|---|---|---|
| 4,237,186 A | * | 12/1980 | Ingraham ................. | B05D 7/20 428/458 |
| 4,282,905 A | | 8/1981 | Dopkin et al. | |

(Continued)

*Primary Examiner* — Michael A Tolin
(74) *Attorney, Agent, or Firm* — Bradley J. Thorson; DeWitt LLP

(57) ABSTRACT

A tube used or medical or other purposes is concentrically bonded to an inner lining tube by sequentially inserting a core within the inner lining tube, creating an adhesive layer on the outer surface of the inner lining tube, inserting the inner lining tube and core into the lumen of the outer tube, and then activating the adhesive to bond the inner tune to the outer tube before removing the core.

19 Claims, 2 Drawing Sheets

(51) Int. Cl.
*C09J 127/18* (2006.01)
*C09J 153/00* (2006.01)
*C09J 175/04* (2006.01)
*B29C 48/00* (2019.01)
*B29C 65/00* (2006.01)
*B29C 63/00* (2006.01)

(56) References Cited

U.S. PATENT DOCUMENTS

| | | |
|---|---|---|
| 5,180,458 A | 1/1993 | White |
| 5,205,886 A | 4/1993 | White |
| 2006/0137757 A1 | 6/2006 | McKeen et al. |
| 2007/0089797 A1 | 4/2007 | Farnsworth |
| 2007/0095473 A1 | 5/2007 | Farnsworth et al. |
| 2017/0043060 A1 | 2/2017 | Wang et al. |
| 2017/0106166 A1 | 4/2017 | Wang et al. |
| 2019/0160259 A1* | 5/2019 | Cottone ............. A61M 25/0113 |

* cited by examiner

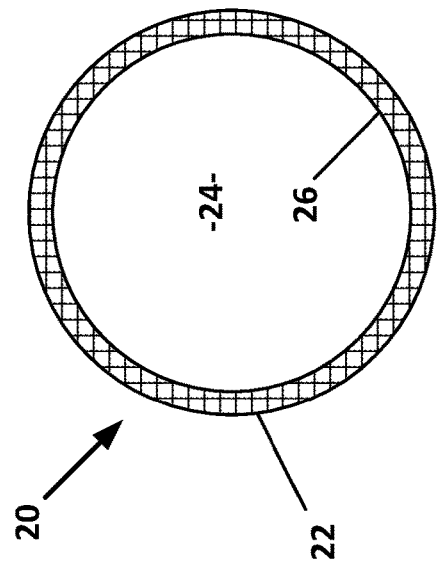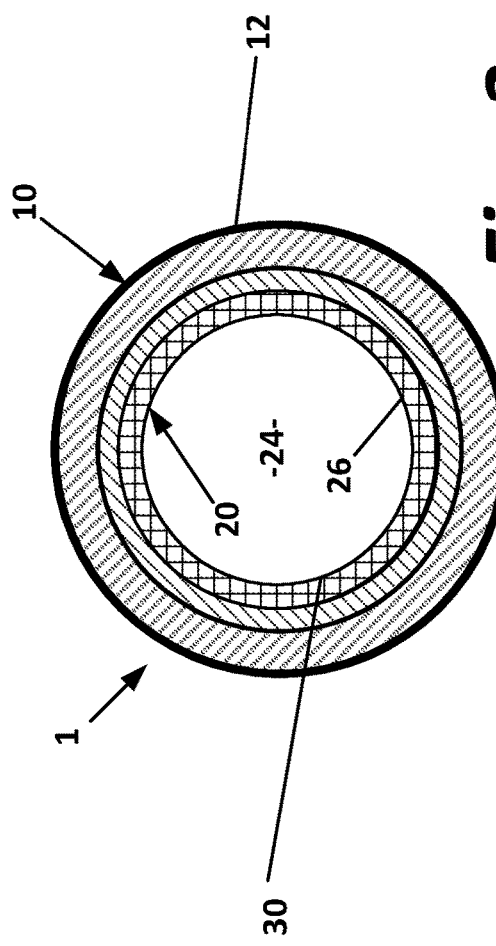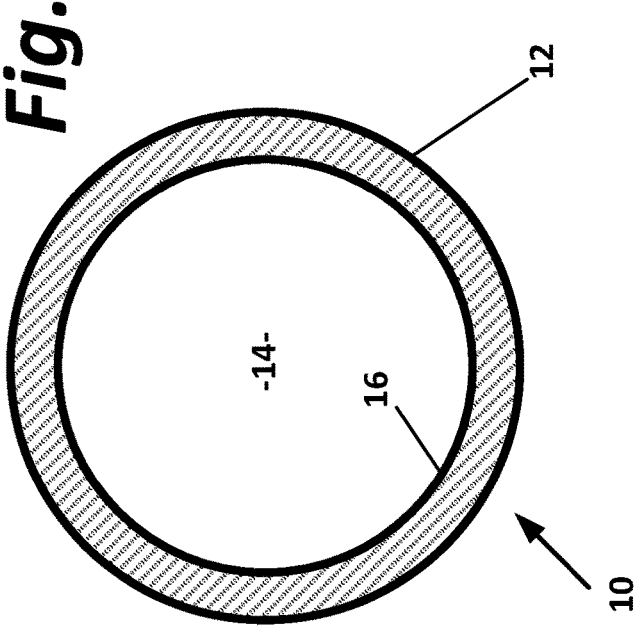

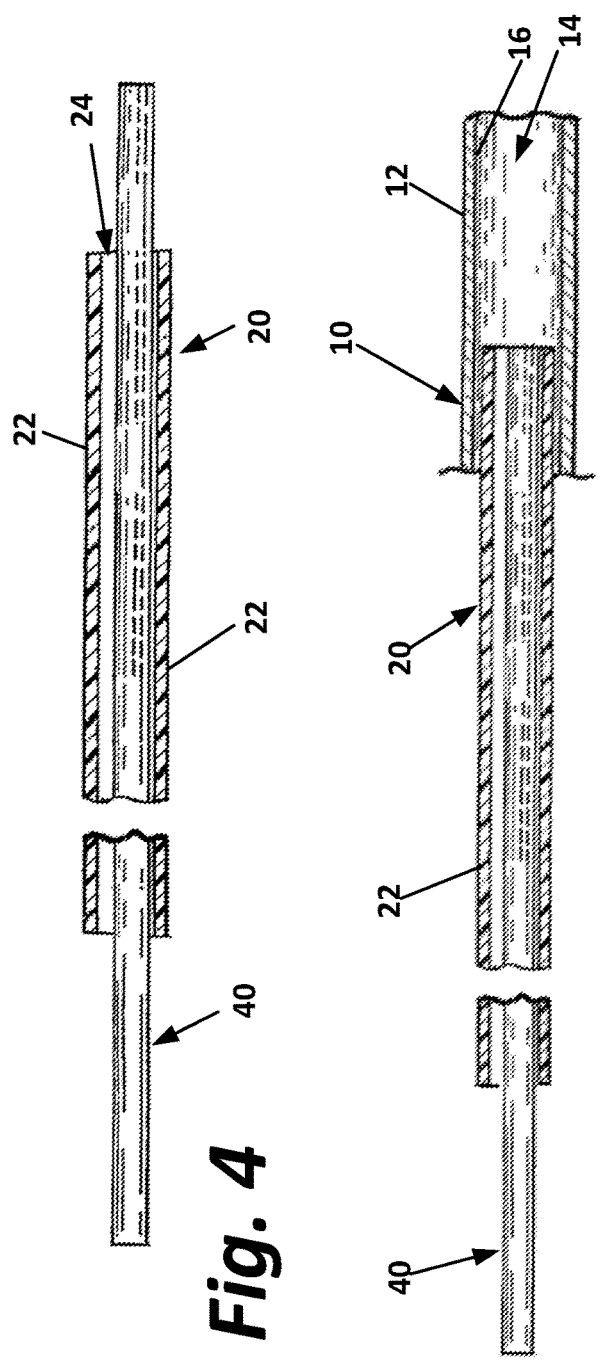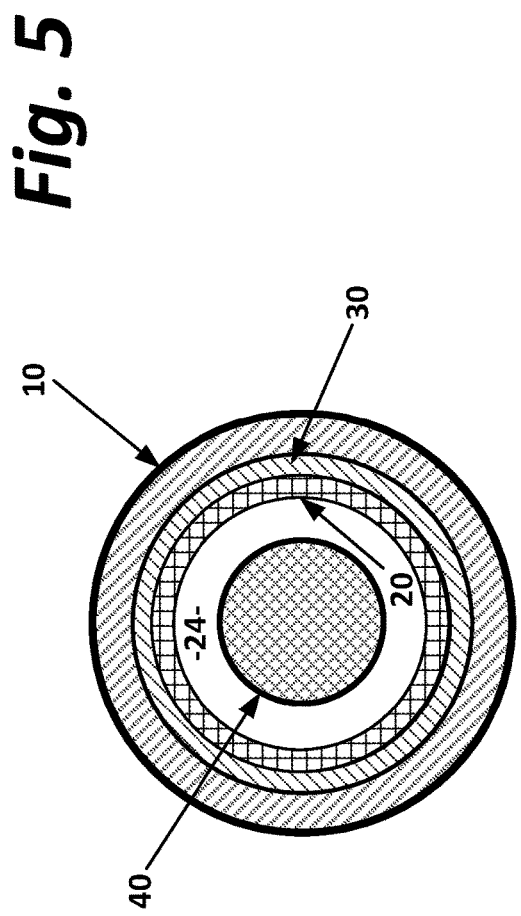

PROCESS FOR CONCENTRICALLY BONDING TUBES USING A HOT MELT ADHESIVE

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates to the production of assemblies comprising two or more concentric tubes. More specifically, the present invention relates to the production of such assemblies comprising a tubular polytetrafluoroethylene (PTFE) liner bonded to the inner wall of another tube using a hot melt adhesive.

PTFE is a high-molecular-weight polymer consisting wholly of carbon and fluorine. PTFE is tough, flexible, hydrophobic material that is chemically inert and has one of the lowest coefficients of friction of any solid. These properties make PTFE ideally suited for various applications. PTFE is used as a non-stick coating for pans and other cookware, as a lubricant for machine parts, and as a graft material in surgical products. PTFE is also frequently employed as a coating on catheters to prevent bacteria and other infectious agents from adhering to the catheters and cause hospital-acquired infections. PTFE has also been used as a liner for industrial pipelines carrying acids, alkalis or other chemicals, and hoses carrying highly viscous liquids.

According to U.S. Pat. No. 4,282,905 granted on Aug. 11, 1981, to Dopkin et al., steel pipes loose-lined with PTFE liners are commercially available. This patent further discloses that discloses PTFE linings have been bonded to the inside of iron pipe using adhesives, heat and applied air pressure. The Dopkin et al. patent itself teaches forming a laminated pipe by placing a tube of PTFE within a close-fitting seamless sleeve of fabric made from an inert fiber and then (i) heating the tube to the softening temperature of the polymer, (ii) expanding the softened tube by inflation or centrifugal force, thereby forcing the softened polymer between the interstices of the fabric sleeve; and finally (iii) cooling the tube while polymer is still within the sleeve so that an integral pipe is formed by means of a bond between the polymer and the fabric. While this method will work to bond a PTFE tube to such a fabric sleeve having interstices, there remains a real need for a process and method that may be used to bond a PTFE liner to the inner wall of a tube not having such interstices.

SUMMARY OF THE INVENTION

Successful and efficient concentric bonding of tubes is achieved by providing a first outer tube and second tube inner tube. The first outer tube has a first outside surface of a first outer diameter, and a first lumen defined by a first inside surface of a first inner diameter. The first outer tube may be made of any suitable material and, for example, may be a metal hypotube of a catheter system. Such a hypotube may be laser cut. The second inner tube may be made from a fluoropolymer, such as PTFE. The second inner tube has a second outside surface and a second outside diameter smaller than the first inside diameter of the first outer tube. The second inner tube also has a second lumen defined by a second inside surface of a second inside diameter.

The first outer tube and the second inner tube are bonded together by inserting a core into the second lumen and temporarily securing the second tube in place on the core. The core and the second tube are then fed through an extrusion apparatus adapted to create an adhesive layer on the second outside surface of the inner tube. Then, the second inner tube is inserted into the first lumen of the first outer tube so that the second outside surface of the second inner tube is in face-to face registration with the first inside surface of the first outer tube with the adhesive layer residing there between. A heat source is then applied to melt (i.e., soften) the adhesive without damaging either of the first tube and the second tube. The heat source is then removed thereby allowing the adhesive to cool and form a bond between the first inside surface of the first outer tube and the second outside surface of the second inner tube.

Various adhesive materials may be used to bond the two tubes together. The adhesive can be PTFE or any of a variety of thermoplastic elastomers such as a thermoplastic polyurethane material, or a thermoplastic polyether block amide material (e.g., such as PEBAX® sold by ARKEMA FRANCE of Puteaux, France). In some cases, thermoset elastomers may also be used without deviating from the invention.

The process for concentrically bonding tubes often comprises additional steps such as removing the core from the second lumen, and wiping the outer surface of the inner tube with a solvent, such as alcohol or equivalent polar solvent, to improve bonding when the inner tube is made of PTFE. The first outer tube of a first predetermined length may be provided. Likewise, a second outer tube is of a second predetermined length may be provided. Alternatively, cutting the second tubes to length may be additional steps in the process. Further, cutting the core at one or both ends may prove advantageous either prior to running the core and second inner tube through the extruder or to facilitate removal of the core from the second lumen.

BRIEF DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts:

FIG. 1 is a cross-sectional view of a first outer tube;

FIG. 2 is a cross-sectional view of a second inner tube;

FIG. 3 is a cross-sectional view of the first outer tube of FIG. 1 and the second inner tube of FIG. 2 concentrically aligned and bonded together by an adhesive;

FIG. 4 is a cross-sectional view of the second inner tube surrounding a core;

FIG. 5 is a cross-sectional view showing the inner second tube and core of FIG. 4 being inserted into an outer tube;

FIG. 6 is a cross-sectional view of the assembly of FIG. 5.

DESCRIPTION OF THE PREFERRED EMBODIMENT

This description of the preferred embodiments is intended to be read in connection with the accompanying drawings, which are to be considered part of the entire written description of this invention. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawings under discussion. These relative terms are for convenience of description and do not require that the apparatus be constructed or operated in a particular orientation. Terms such as "connected," "connecting," "attached," "attaching," "join" and "joining" are used interchangeably and refer to one structure or surface being secured to another structure or surface or integrally fabricated in one piece, unless expressively described otherwise.

FIGS. 1 through 3 show the parts of an assembly 1 comprising a first outer tube 10 lined with a second inner tube 20. The first outer tube 10 and the second inner tube 20 are arranged concentrically and the second inner tube 20 is bonded to the first outer 10 by an adhesive layer 30 as shown in FIG. 3. The first outer tube 10 is shown as having a first outside surface 12 of a first outer diameter, and a first lumen 14 defined by a first inside surface 16 and having a first inner diameter. The second inner tube 20 has a second outside surface 22 of a second outer diameter that is smaller than the first inner diameter of the first lumen 14. The second inner tube 20 also has a second lumen 24 defined by a second inside surface 26 and having a second inner diameter. The adhesive layer 30 resides between the first inside surface 16 and the second outside surface 22.

The materials employed to construct the first outer tube 10, the second inner tube 20 and the adhesive layer 30 may vary depending on the specific use of the assembly 1. The first outer tube 10 may be constructed of suitable metal such as stainless steel, nickel, platinum, platinum alloys, titanium, cobalt chromium, or a nickel-cobalt alloy. When made of such materials, the tube may be left rigid and intact, or laser cut for flexibility. The first outer tube 10 may also be made of a shape-memory metallic materials such as nitinol. Suitable thermoplastic materials may also be used when forming the first outer tube. Such plastic materials include polyvinyl chloride, silicone rubber, latex, polyurethane, polyethylene terephthalate, polytetrafluoroethylene (PTFE). and other thermoplastic elastomers.

While various materials may also be employed to construct the second inner tube 20, a high-molecular-weight fluoropolymer is preferred and particularly a fluoropolymer. That is tough, flexible, hydrophobic, chemically inert and has a low coefficient of friction. PTFE meets all these requirements. The adhesive layer 30 may also be made from PTFE or any of a variety of thermoplastic elastomers such as a polyurethane material, or a thermoplastic polyether block amide material such as PEBAX® sold by ARKEMA FRANCE of Puteaux, France.

The assembly shown in FIGS. 1 through 3 is constructed using the novel steps described below.

The first step, of course, if to secure a first outer tube 10 and a second inner tube 20, each appropriately sized and made of a suitable material. As shown in FIG. 4, a core 40 is also provided. The core 40 will ideally be relatively stiff, elongate and have an outside diameter significantly smaller than the inside diameter of the inside surface 26 and second lumen 24 of the second inner tube 20. This allows a substantial portion of the core 40 to be inserted into the second lumen 24. The relative sizes of the outer diameter of the core 40 and the inner diameter of the second inner tube 20 also may make it necessary to temporarily secure the core 40 in place within the second inner tube 20 using pieces of a suitable tape (not shown) coupled to the core 40 on opposite ends of the second inner tube 20.

After the core 40 and the second inner tube 20 have been assembled as shown in FIG. 4, the adhesive layer 30 is created on the outer surface 22 of the second inner tube 20. This step is best performed by feeding the core 40 and the second inner tube 20 through an extrusion apparatus that is adapted to create the adhesive layer 30 on the outer surface 22. The term "create" is used broadly to include either treating the outer surface 22 of the second inner tube 20 to provide the outer surface 22 with adhesive characteristics or applying a separate adhesive material to the outer surface 22 of the second inner tube 20. In either case, the adhesive layer 30 will either temporarily harden or be sufficiently viscous to prevent the adhesive layer 30 from sluffing off the outer surface 22 during the remainder of the manufacturing process.

More specifically, application of the adhesive layer may be performed using an annular die crosshead assembly attached to an extruder having several heat zones and two pressure sensors coupled to a pressure loop controller. The extruder is used with sleaving tooling and a sizing calibrator. The extrusion step typically also includes the use of a water quenching tank, a laser gauging system, a puller/cutter, and a catch tray.

The adhesive layer is created by loading the second inner tube 20 onto the precision core 40 and held in place on the core 40 by applying one revolution of tape or some other adherable material about the front end of the second inner tube 20 and the portion of the core 40 extending from and immediately adjacent the front end to second inner tube 20. This assembly of the core 40 and second inner tube 20 is then fed through the extrusion crosshead after (a) each heat zone of the extruder has been individually preheated to a desired temperature, (b) the die pressure and the head pressure have been set, and (c) the speed of the puller has been set. The puller and the other equipment of the extrusion system are calibrated so that as the core 40 and the second inner tube 20 are pulled through the extruder, an annular bead of adhesive of a predetermined gauge thickness is applied to the outer surface of the second inner tube. For example, the combined diameter of the second inner tube 40 and the adhesive layer 30 may be 0.002 to 0.005 inches smaller than the diameter of the lumen 14 of the first outer tube 10.

As illustrated in FIGS. 5 and 6, after the adhesive layer 30 is in place on the second outer surface 22 of the second inner tube 20, the core 40 and second inner tube 20 are inserted through the first lumen 14 of the first outer tube 10. This places the first inside surface 16 of the first outer tube 10 in face-to-face registration with the second outside surface 22 of the second inner tube 20 with the adhesive layer 30 therebetween. See FIG. 3. A heat source is then applied to the assembly to activate the adhesive layer 30. For example, the heat source serves to hot melt the adhesive layer 30 without damaging either the first outer tube 10 or the second inner tube 20. The heat source is then removed thereby allowing the adhesive layer 30 to cool and form a bond between the first inside surface 16 of the first outer tube 10 and the second outside surface 22 of the second inner tube 20. Once this bond has been created, the core 40 is removed and the assembly is trimmed to length and sanitized.

The components may be trimmed to length either before or after removal of the core without deviating from the invention. Likewise, the first outer tube 10 and the second inner tube 20 may already be of a predetermined length such that the trimming step is unnecessary. When certain materials are employed, it may prove advantageous to pre-treat the tubes 10/20 prior to application of the adhesive layer. For example, when either of the tubes is constructed of PTFE, it is advantageous to wipe the surface to be bonded with a solvent such as alcohol or an equivalent polar solvent.

The methods and materials described above have broad application, but have proven to be well-suited for the construction of hypotubes used in catheter systems. Lining a metal or plastic laser cut hypotube with an inner PTFE tube as described above makes the inside of the assembly more lubricious such that it is easier to pass medical instruments through the hypotube during interventional medical procedures. Such a PTFE inner tube also acts as barrier preventing bacteria and other infectious agents from adhering to the catheters and other tubing used in hospitals reducing the risk of hospital-acquired infections. While an assembly of two concentric tubes is shown and described, the process described above may also be employed to add more tubes to the assembly. Such additional tubes may have a smaller outside diameter than the diameter lumen 24 or a lumen larger in diameter than the outside diameter of tube 10.

It should be understood that, within the scope of the following claims, the invention may be practiced otherwise than as specifically shown in the drawings and described above. The foregoing description is intended to explain the various features and advantages, but is not intended to be limiting. The scope of the invention is defined by the following claims which are also intended to cover a reasonable range of equivalents.

The invention claimed is:

1. A process for concentrically bonding tubes comprising:
   a. providing a first outer tube having a first outside surface of a first outer diameter, and a first lumen defined by a first inside surface of a first inner diameter;
   b. providing a second tube made from a fluoropolymer and having a second outside surface of a second outer diameter, said second outer diameter being smaller than the first inner diameter, and a second lumen defined by a second inside surface of a second inner diameter;
   c. inserting a core into the second lumen and temporarily securing the second tube in place on the core;
   d. feeding the core and the second tube through an extrusion apparatus adapted to create an adhesive layer on the second outside surface;
   e. inserting the second tube into the first lumen so that the second outside surface is in face-to face registration with the first inside surface with the adhesive layer residing there between; and
   f. applying a heat source to melt the adhesive layer without damaging either of the first tube and the second tube, and then removing the heat source thereby allowing the adhesive layer to cool and form a bond between the first inside surface and the second outside surface.

2. The process for concentrically bonding tubes of claim 1, wherein said fluoropolymer is polytetrafluoroethylene (PTFE).

3. The process for concentrically bonding tubes of claim 2, further comprising the step of wiping the PTFE with a solvent.

4. The process for concentrically bonding tubes of claim 3, wherein said solvent is alcohol.

5. The process for concentrically bonding tubes of claim 1, wherein said adhesive is made of a thermoplastic elastomer.

6. The process for concentrically bonding tubes of claim 1, wherein said adhesive layer is made of a material selected from a group consisting of PTFE, polyurethane, and polyether block amide.

7. The process for concentrically bonding tubes of claim 1, further comprising the step of removing the core from the second lumen.

8. The process for concentrically bonding tubes of claim 1, further comprising the step of cutting the second tube and the core at both ends and removing the core from the second lumen.

9. The process for concentrically bonding tubes of claim 1, wherein said first outer tube is a hypotube.

10. The process for concentrically bonding tubes of claim 1, wherein said first outer tube is a laser cut hypotube.

11. The process for concentrically bonding tubes of claim 10, wherein said hypotube is made of a metal.

12. The process for concentrically bonding tubes of claim 1, wherein said first outer tube is of a first predetermined length.

13. The process for concentrically bonding tubes of claim 1, wherein said second outer tube is of a second predetermined length.

14. A process for concentrically bonding tubes comprising:
   a. providing a first metal hypotube of a first predetermined length and having a first outside surface of a first outer diameter, and a first lumen defined by a first inside surface of a first inner diameter;
   b. providing a second tube of a second predetermined length, said second tube made from polytetrafluoroethylene (PTFE) and having a second outside surface of a second outer diameter, said second outer diameter being smaller than the first inner diameter, and a second lumen defined by a second inside surface of a second inner diameter;
   c. inserting a core into the second lumen and temporarily securing the second tube in place on the core;
   d. feeding the core and the second tube through an extrusion apparatus adapted to create an adhesive layer on the second outside surface;
   e. inserting the second tube into the first lumen so that the second outside surface is in face-to face registration with the first inside surface with the adhesive layer residing there between; and
   f. applying a heat source to melt the adhesive layer without damaging either of the first tube and the second tube, and then removing the heat source thereby allowing the adhesive layer to cool and form a bond between the first inside surface and the second outside surface.

15. The process for concentrically bonding tubes of claim 14, wherein said adhesive layer is made of a thermoplastic elastomer.

16. The process for concentrically bonding tubes of claim 14, wherein said adhesive layer is made of a material selected from a group consisting of PTFE, polyurethane, and polyether block amide.

17. The process for concentrically bonding tubes of claim 14, further comprising the step of removing the core from the second lumen.

18. The process for concentrically bonding tubes of claim 14, further comprising the step of cutting the second tube and the core at both ends and removing the core from the second lumen.

19. The process for concentrically bonding tubes of claim 14, further comprising the step of wiping the PTFE with alcohol.

\* \* \* \* \*